(12) United States Patent
Jossifoff

(10) Patent No.: US 7,393,543 B2
(45) Date of Patent: Jul. 1, 2008

(54) VAGINALLY ADMINISTRATABLE PROGESTERONE-CONTAINING TABLETS AND METHOD FOR PREPARING SAME

(75) Inventor: Azariah Jossifoff, Ramat Gan (IL)

(73) Assignee: Ferring B.V., Hoofddorp (NL)

(*) Notice: Subject to any disclaimer, the term of this patent is extended or adjusted under 35 U.S.C. 154(b) by 265 days.

(21) Appl. No.: 10/832,742

(22) Filed: Apr. 26, 2004

(65) Prior Publication Data
US 2005/0008694 A1 Jan. 13, 2005

Related U.S. Application Data

(63) Continuation of application No. 09/856,417, filed on Aug. 8, 2001, which is a continuation of application No. PCT/IL99/00619, filed on Nov. 17, 1999.

(30) Foreign Application Priority Data
Nov. 18, 1998 (IL) .................................. 127129

(51) Int. Cl.
A61F 13/00 (2006.01)
A61K 9/46 (2006.01)

(52) U.S. Cl. .................................. 424/434; 424/466

(58) Field of Classification Search ................ 424/434, 424/489, 466
See application file for complete search history.

(56) References Cited

U.S. PATENT DOCUMENTS

| | | | |
|---|---|---|---|
| 3,121,663 A | 2/1964 | Parker | |
| 4,310,510 A * | 1/1982 | Sherman et al. | 424/45 |
| 4,853,211 A * | 8/1989 | Kurobe et al. | 424/433 |
| 5,084,277 A * | 1/1992 | Greco et al. | 424/433 |
| 5,116,619 A | 5/1992 | Greco et al. | |
| 5,543,150 A | 8/1996 | Bologna et al. | |
| 5,958,455 A * | 9/1999 | Roser et al. | 424/489 |
| 5,993,856 A | 11/1999 | Ragavan et al. | |
| 6,086,916 A | 7/2000 | Agnus et al. | |
| 9,856,417 * | 8/2001 | Jossifoff | 424/434 |
| 2005/0181045 A1* | 8/2005 | Jossifoff | 424/464 |
| 2006/0188571 A1* | 8/2006 | Jossifoff | 424/464 |

OTHER PUBLICATIONS

Chakmkjian et al (J. of Reproductive Medicine, 1987, 3(6), 443-8).*
U.S. Appl. No. 11/557,036, filed Nov. 2006, Yankov et al.*
Bulletti, C. et al., Targeted drug delivery in gynaecology: the first uterine pass effect, Human Reproduction, 1997, vol. 12, pp. 1073-1079.
Ficiciouglu, C. et al., High local endometrial effect of vaginal progesterone gel, Gynecol Endocrinol., 2004, vol. 18, pp. 240-243.
Levy, T. et al., Pharmacokinetics of natural progesterone administered in the form of a vaginal tablet, Human Reproduction, 1999, vol. 14, pp. 606-610.
Levy, T. et al., Pharmacokinetics of the progesterone-containing vaginal tablet and its use in assisted reproduction, Steroids, 2000, vol. 65, pp. 645-649.
Lewin, A. et al., Simplified artificial endometrial preparation, using oral estradiol and novel vaginal progesterone tablets: a prospective randomized study, Gynecol Endocrinol, 2002, vol. 15, pp. 131-136.
Maymon, R. and Schulman, A., Comparison of triple serum screening and pregnancy outcome in oocyte donation versus IVF pregnancies, Human Reproduction, 2001, vol. 16, pp. 691-695.
Schulman, A. et al., The best donor, Human Reproduction, 1999, vol. 14, pp. 2493-2496.

* cited by examiner

*Primary Examiner*—Alton Pryor
(74) *Attorney, Agent, or Firm*—Darby & Darby P.C.

(57) ABSTRACT

The present invention provides a method for preparing a tablet for the vaginal administration of progesterone for systemic use. The method comprises first mixing water with micronized progesterone, the total amount of water mixed with said micronized progesterone not exceeding the maximum wetting capacity of the micronized progesterone; drying the wetted, micronized progesterone; mixing the dry micronized progesterone with other pharmaceutically acceptable excipients or diluents; and; forming a tablet by direct compaction of the dry micronized progesterone. Tablets prepared by this method are also provided.

24 Claims, No Drawings

VAGINALLY ADMINISTRATABLE PROGESTERONE-CONTAINING TABLETS AND METHOD FOR PREPARING SAME

This application claims priority from U.S. application Ser. No. 09/856,417 filed Aug. 8, 2001, and from International Application PCT/IL99/00619 filed Nov. 17, 1999, each of these prior applications is incorporated herein by reference in its entirety.

FIELD OF THE INVENTION

The invention relates to the preparation of pharmaceutical compositions containing progesterone, in particular to compositions for vaginal delivery of progesterone.

BACKGROUND OF THE INVENTION

Since its discovery in the 1950's, synthetic oral progesterone has been used for a variety of gynecological conditions. However, androgenic activity inherent in the synthetic compound precludes its liberal use in assisted reproductive technology (ART) because of the threat of teratogenic effects.

Furthermore, synthetic progesterone used in hormonal replacement therapy (HRT) may partially reverse the estrogenic benefits on the cardiovascular system and lipoprotein metabolism (Lobo, Am. J. Obstet. Gynecol. 166 (1992), 1997-2004; Fahraeus et al., Eur. J. Clin. Invest. 13 (1983), 447-453; Ottosson et al., Am. J. Obstet. Gynecol. 151 (1985), 746-750; Knopp, Am. J. Obstet. Gynecol. 158 (1988), 1630-1643; Crook et al., 166 (1992) 950-954).

Natural progesterone is devoid of any androgenic activity that might compromise lipoprotein metabolism or induce teratogenicity. Moreover, it probably has a direct beneficial effect on blood vessels (Jiang et a]., Eur. J. Pharmacol. 211 (1992), 163-167).

The major difficulty in utilizing natural progesterone is its route of administration. Oral intake is hampered by rapid and extensive intestinal and liver metabolism, leading to poorly sustained serum levels and low bioavailability (Adlercreutz et al., J. Steroid Biochem. 13 (1980), 231-244; Arafat et al., Am. J. Obstet. Gynecol. 159 (1988), 1203-1209; Whitehead et al., Brit. Med. J. 280 (1980), 825-827; Ottosson et al., Br. J. Obstet. Gynecol. 91 (1984), 11 11-1119; Padwick et al., Fertil. Steril. 46 (1986), 402-407; Nahoul et al., Maturitas 16 (1993), 185-202; Nillus et al., Am. J. Obstet. Gynecol. 110 (1971), 470-477; Chakmakjian et al., J. Reprod. Med. 32 (1987), 443-448). Intramuscular injection assures reliable absorption, but is painful, can cause local irritation and cold abscesses (Devroey et al., Int. J. Fertil. 34 (1989), 188-193), must be administered by trained medical personnel, and often suffers from low patient compliance.

For these reasons, the vaginal route has become the most established way in which to deliver natural progesterone. The progesterone is easily administered to the vagina, which has a large potential of absorption, and also avoids liver first-pass metabolism when delivered to the vagina.

Many vaginal formulations have been assayed, mostly as suppositories (Price et al., Fertil. Steril. 39 (1983), 490-493; Norman et al., Fertil. Steril. 56 (1991), 1034-1039; Archer et al., Am. J. Obstet. Gynecol., 173 (1995), 471-478), gelatin capsules (Devroey et al., Int. J. Fertil. 34 (1989), 188-193; Smitz et al., Hum. Reprod. 2 (1992), 309-314; Miles et al., Fertil. Steril. 62 (1994), 485-490), and recently as bio-adhesive gels (Fanchin et al., Obstet. Gynecol. 90 (1997), 396-401; Ross et al., Am. J. Obstet. Gynecol. 177 (1997), 937-941).

Although the suppositories are easily inserted, they melt at body temperature and lead to disturbing vaginal discharge. Oral gelatin capsule containing micronized progesterone have also been used vaginally (Devroey et al., Int. J. Fertil. 34 (1989), 188-193; Smitz et al., Hum. Reprod. 2 (1992), 309-314; Miles et al., Fertil. Steril. 62 (1994), 485-490), but insertion of a small capsule high into the vagina is difficult and large doses of 600 to 800 mg are needed to achieve adequate plasma concentration (Smitz et al., Hum. Reprod. 2 (1992), 309-314; Miles et al., Fertil. Steril. 62 (1994), 485-490; Bourgain et al., Hum. Reprod. 5 (1990), 537-543).

U.S. Pat. Nos. 5,084,277 and 5,116,619, both to Greco et al., disclose a process for the preparation of a progesterone-containing tablet and tablets so prepared. The Greco et al. process involves wet granulation of progesterone into the tablets. As is well-known in the art, wet granulation processes necessitate several steps in the formulation of the resulting tablets. These steps add considerably to the production costs of tablets produced by wet granulation methods, particularly in comparison to comparable "direct compaction" methods, in which the material of interest is tabletted while dry and which involve fewer steps than wet-granulation methods. Greco et al. employs a wet granulation technique because commercially available progesterone has bulk properties which render it unsuitable for direct compaction in the concentrations necessary for use in ART (typically about 50-100 mg progesterone per 1000 mg tablet). Greco gives no suggestion as to how one might be able to tablet progesterone via a direct-compaction method, which is economically more desirable.

The use of a wet granulation method in the preparation of progesterone-containing tablets also precludes incorporation of an effervescent into the tablet. If the tablet is to be vaginally administered, incorporation of an effervescent would be helpful, since the effervescent would aid in the dissolution of the tablet and absorption of the progesterone into the bloodstream.

SUMMARY OF THE INVENTION

The present invention seeks to provide a method for the production of a tablet for the vaginal delivery of progesterone as well as tablets containing progesterone.

There is thus provided, in accordance with a preferred embodiment of the invention, a method for preparing a tablet for the vaginal administration of progesterone for systemic use, comprising the steps of:

slowly mixing water with micronized progesterone, the total amount of water mixed with said micronized progesterone not exceeding the maximum wetting capacity of the micronized progesterone, whereby to obtain wetted micronized progesterone;

drying said wetted micronized progesterone to a humidity content of substantially 0%, whereby to form substantially dry micronized progesterone;

mixing said substantially dry micronized progesterone with other pharmaceutically acceptable excipients or diluents therefor; and forming a tablet by direct compaction of said substantially dry micronized progesterone which has been mixed with said other pharmaceutically acceptable excipients or diluents therefor.

There is also provided, in accordance with another preferred embodiment of the invention, a method for preparing a tablet for the vaginal administration of progesterone for systemic use, comprising the steps of:

slowly mixing water with micronized progesterone, the total amount of water mixed with said micronized progesterone not exceeding the maximum wetting capacity of the micronized progesterone, whereby to obtain wetted micronized progesterone;

drying said wetted micronized progesterone to a humidity content of substantially 0%, whereby to form substantially dry micronized progesterone;

mixing said substantially dry micronized progesterone with other pharmaceutically acceptable excipients or diluents therefor, including an effervescent; and forming a tablet by direct compaction of said substantially dry micronized progesterone which has been mixed with said other pharmaceutically acceptable excipients or diluents therefor, including an effervescent.

There is further provided, in accordance with another preferred embodiment of the invention, a method for preparing a tablet for the vaginal administration of progesterone for systemic use, comprising the steps of:

slowly mixing water with micronized progesterone, the total amount of water mixed with said micronized progesterone does not exceed the maximum wetting capacity of the amount of micronized progesterone, whereby to obtain wetted micronized progesterone;

drying said wetted micronized progesterone to a humidity content of substantially 0%, whereby to form substantially dry micronized progesterone;

sieving a first lubricant to obtain a sieved first lubricant;

mixing said substantially dry micronized progesterone with said sieved first lubricant and a material selected from a first filler or a disintegrant to form a first mixture;

mixing a binder which binds dry particles with said first mixture to form a second mixture;

intimately mixing an effervescent and a first quantity of a second filler to form a third mixture;

sieving said third mixture to obtain a sieved third mixture, and then intimately mixing said sieved third mixture and said second mixture to form a fourth mixture;

intimately mixing the fourth mixture with a second quantity of said second filler to form a fifth mixture;

sieving a second lubricant and a material selected from a saponificant or a third lubricant to obtain, respectively, sieved second lubricant and sieved third lubricant;

intimately mixing said sieved second lubricant and said sieved third lubricant with said fifth mixture to form a sixth mixture; and tabletting said sixth mixture by direction compaction to form a tablet.

In a preferred embodiment of the invention, the amount of water mixed with the micronized progesterone is between about 25 and 28 wt. % of the amount of micronized progesterone.

In another preferred embodiment of the invention, the water is added to the micronized progesterone at rate of between about 6-9 ml per minute, at a mixing speed of between about 25-33.3 rpm.

In another preferred embodiment of the invention, the first lubricant is sieved through sieves having a pore size of between about 400 and 450 microns, preferably about 425 microns.

In another preferred embodiment of the invention, the third mixture is sieved through sieves having a pore size of between about 400 and 450 microns, preferably about 425 microns prior to mixing with the second mixture.

In another preferred embodiment of the invention, said sieved second lubricant and said sieved third lubricant are sieved through sieves having a pore size of between about 100 and 150 microns, preferably 125 microns prior to mixing with said fifth mixture.

In one preferred embodiment of the invention, said drying of said wetted micronized progesterone is done at a temperature of between about 55° C. and about 60° C.

In another preferred embodiment of the invention, all of said mixing steps are carried out at a temperature of between about 15° C. and 30° C.

In one preferred embodiment of the invention, said first lubricant is silicon dioxide (colloidal anhydrous silica).

In another preferred embodiment of the invention, said material selected from a first filler or a disintegrant is a starch exhibiting good flow properties, such as cornstarch 1500 or other starches derived from corn (maize), potatoes or wheat, as are well known in the art.

In a preferred embodiment of the invention, the binder which binds dry particles is polyvinylpyrrolidone (povidone), e.g. Povidone 30.

In another preferred embodiment of the invention, said second filler is derived from a natural source and is more preferably lactose or is composed principally of lactose (e.g. ludipress, which as is well known in the art is a commercially available mixture of polyvinylpyrrolidone and lactose).

In a preferred embodiment of the invention, said effervescent is a mixture of a pharmaceutically acceptable carboxylic or dicarboxylic acid, such as adipic acid or tartaric acid, and a pharmaceutically acceptable salt of $HCO_3^-$, such as sodium bicarbonate. Preferably the acid and bicarbonate are present in an amount providing a molar excess of —COOH groups.

In another preferred embodiment of the invention, said first portion and said second portion of said second filler are of generally the same size.

In one preferred embodiment of the invention, the effervescent is prepared prior to said intimate mixing of said first portion of said second filler with said effervescent. In another preferred embodiment of the invention, said effervescent is prepared in situ as part of said intimate mixing of said first portion of said second filler with said effervescent.

In a preferred embodiment of the invention, said intimate mixing of said first portion of said second filler with said effervescent comprises non-intimately mixing said first portion of said second filler with said effervescent and passing the resultant non-intimately mixed mixture through a sieve having an average pore size between about 400 and 450 microns, preferably about 425 microns diameter to obtain said third mixture.

In a preferred embodiment of the invention, the effervescent comprises between about 6 and 10 wt. %, preferably about 8 wt. % of the tablet.

In one preferred embodiment of the invention, said intimate mixing of said second mixture with said third mixture to obtain said fourth mixture is accomplished by non-intimately mixing said second mixture with said third mixture to obtain a non-intimately mixed mixture and sifting said non-intimately mixed mixture through a sieve having an average pore size between about 400 and 450 microns, preferably about 425 microns diameter to obtain said fourth mixture.

In a preferred embodiment of the invention, said second lubricant is selected from magnesium stearate, talc, sodium lauryl sulfate, and phosphates known in the art to function as lubricants.

In another preferred embodiment of the invention, said material selected from a saponificant or a third lubricant is sodium lauryl sulfate.

There is also provided in accordance with another preferred embodiment of the invention a tablet prepared by the steps of: slowly mixing water with micronized progesterone, the total amount of water mixed with said micronized progesterone not exceeding the maximum wetting capacity of the amount of micronized progesterone, whereby to obtain wetted micronized progesterone; drying said wetted micronized progesterone to a humidity content of substantially 0%, whereby to form substantially dry micronized progesterone; mixing said substantially dry micronized progesterone with other pharmaceutically acceptable excipients or diluents therefor; and forming a tablet by direct compaction of said substantially dry micronized progesterone which has been mixed with said other pharmaceutically acceptable excipients or diluents therefor.

There is also provided in accordance with another preferred embodiment of the invention a tablet prepared by the steps of: slowly mixing water with micronized progesterone, the total amount of water mixed with said micronized progesterone not exceeding the maximum wetting capacity of the amount of micronized progesterone, whereby to obtain wetted micronized progesterone; drying said wetted micronized progesterone to a humidity content of substantially 0%, whereby to form substantially dry micronized progesterone; mixing said substantially dry micronized progesterone with other pharmaceutically acceptable excipients or diluents therefor, including an effervescent; and forming a tablet by direct compaction of said substantially dry micronized progesterone which has been mixed with said other pharmaceutically acceptable excipients or diluents therefor, including an effervescent.

There is also provided in accordance with another preferred embodiment of the invention a tablet prepared by the steps of: slowly mixing water with micronized progesterone, the total amount of water mixed with said micronized progesterone not exceeding the maximum wetting capacity of the amount of micronized progesterone, whereby to obtain wetted micronized progesterone; drying said wetted micronized progesterone to a humidity content of substantially 0%, whereby to form substantially dry micronized progesterone; sieving a first lubricant to obtain a sieved first lubricant; mixing said substantially dry micronized progesterone with said sieved first lubricant and a material selected from a first filler or a disintegrant to form a first mixture; mixing a binder which binds dry particles with said first mixture to form a second mixture; intimately mixing an effervescent and a first quantity of a second filler to form a third mixture; sieving said third mixture to obtain a sieved third mixture, and then intimately mixing said sieved third mixture and said second mixture to form a fourth mixture; intimately mixing the fourth mixture with a second quantity of said second filler to form a fifth mixture; sieving a second lubricant and a material selected from a saponificant or a third lubricant to obtain, respectively, sieved second lubricant and sieved third lubricant; intimately mixing said sieved second lubricant and said sieved third lubricant with said fifth mixture to form a sixth mixture; and tabletting said sixth mixture by direction compaction to form a tablet.

There is also provided in accordance with a preferred embodiment of the invention a tablet comprising between about 6 to 20 wt. % progesterone and between about 5 to 12 wt. % effervescent. In a preferred embodiment of the invention, the tablet comprises between about 8 to 12 wt. % progesterone. In a preferred embodiment of the invention, the tablet comprises between about 6 to 8 wt. % effervescent.

DETAILED DESCRIPTION OF THE PREFERRED EMBODIMENTS

The invention will be better understood through the following illustrative and non-limitative description and examples of preferred embodiments of the invention.

EXAMPLE 1

Preparation of Tablets

Step 1: To 1000 g of micronized progesterone were added 280 g of distilled water, with mixing using a planetary mixer, over a period of 30 minutes. After mixing, the wetted micronized progesterone was spread on pans to thickness of about 4-5 mm, and the pans then placed in an oven at 58° C. The humidity was checked periodically using a humidity checker. When the humidity of the micronized progesterone was reduced to substantially 0%, the dried micronized progesterone was either used immediately in step 2 as described below, or was stored in dry, sealed containers for later use in step 2.

Step 2: Colloidal anhydrous silica (Aerosil 380, 25 g) was sieved through a Russel sieve having pores of 425 micron size, and mixed for 10 minutes with 1000 g of micronized progesterone from Step 1 and 2100 g of maize 1500 starch, using an Angelsman mixer at 32 RPM, to form Mixture A. At the end of the 10 minutes of mixing, 490 g of povidone 30 were added to Mixture A, and mixing was continued for another ten minutes, to prepare "Mixture B".

Step 3: Lactose (Ludipress, BASF, 3800 g), adipic acid (570 g) and sodium bicarbonate (430 g) were mixed for 10 minutes at room temperature using an Angelsman mixer at 32 RPM. Following mixing, these ingredients were sieved through a Russel sieve having pores of 425 microns to obtain "Mixture C".

Step 4: Mixtures B and C were mixed for 10 minutes at room temperature using an Angelsman mixer at 32 RPM to obtain "Mixture D".

Step 5: Mixture D (8415 g) was mixed with 3800 g of lactose (Ludipress) for 10 minutes at room temperature using an Angelsman mixer at 32 RPM, to obtain "Mixture E".

Step 6: Magnesium stearate (230 g) and sodium lauryl sulfate (50 g) were sieved through a Russel sieve (pore size 125 microns). The sieved magnesium stearate and sodium lauryl sulfate were then mixed for with mixture E for 20 minutes at room temperature using an Angelsman mixer, to obtain "Mixture F".

Step 7: Tablets were obtained from mixture F by direct compaction using an Eko Korsch Press. The amounts of ingredients listed in this example are suitable for production of 10,000 tablets each containing about 100 mg progesterone.

EXAMPLE 2

Using the above process, tablets of 1187 mg to 1312 mg total weight, containing from 90 to 110 mg progesterone, were obtained.

EXAMPLE 3

The process described in Example 1 was modified by doubling the amount of filler (Ludipress) to obtain tablets containing on average 50 mg progesterone.

EXAMPLE 4

The pharmacokinetics and clinical use of tablets prepared in accordance with the invention were evaluated as follows: 50 healthy, post-menopausal women with intact uteri, 39 of whom had suffered premature menopause and 11 who were truly postmenopausal, all of whom were undergoing hormone replacement therapy (HRT), submitted blood samples for determination of baseline profiles of hormones (progesterone and other hormones) and other biochemicals (bilirubin, cholesterol, etc.). The blood samples were taken at 8 AM on the first day of the evaluation (day 0) in a fasting state, by intravenous indwelling catheter which was introduced into the cubital vein. Non-estrogen primed postmenopausal women were chosen in order to avoid confusion with endogenous progesterone secretion and estrogen influence on vaginal mucosa absorption (Villanueva et al., Fertil. Steril. 35 (1981), 433-437).

The women then self-administered the progesterone vaginal tablet using a plastic applicator and lay down for 20 minutes. Repeat blood samples for progesterone concentration were withdrawn 0.5, 1, 2, 4, 6, 8, 10, 12 and 24 hours after the vaginal insertion. Blood was allowed to clot at room temperature for 1 hour, after which the serum was separated by centrifugation and stored at −20° C. until analysis.

To evaluate clinical use of the drug, the women were instructed to insert tablets prepared in accordance with the present invention, containing the same dose as administered on day 0, twice daily starting on day 1, and to recline for 20 minutes after each insertion. On days 14 and 30, blood samples for comparison with the baseline were drawn in the morning while the subjects were in a fasting state.

Of the 50 women who participated in the evaluation, 20 were allocated tablets containing 50 mg progesterone, and the remainder of the participants received tablets containing 100 mg progesterone. The baseline details of the participants are summarized in Table I.

TABLE I

|  | Tablets containing 50 mg progesterone | Tablets containing 100 mg progesterone | Total |
|---|---|---|---|
| Median age (years) | 43 ± 6.1 | 43.2 ± 7.9 | 43.3 ± 7.2 |
| Age range (years) | 28-53 | 28-55 | 28-55 |
| Height (cm) | 161.3 ± 8.6 | 161.6 ± 5.7 | 161.5 ± 6.9 |
| Weight (kg) | 67.1 ± 11.5 | 62.8 ± 13.1 | 64.5 ± 12.5 |
| BMI (kg/m²) | 25.9 ± 4.2 | 24.0 ± 4.4 | 24.8 ± 4.4 |

Data are expressed as mean ± standard deviation unless otherwise specified. Body mass index (BMI) was calculated as weight in kg divided by the square of height in meters.

A single vaginal application of a 50 mg progesterone-containing tablet prepared in accordance with the invention resulted in the rapid increase of plasma progesterone concentration. The mean peak plasma level ($T_{max}$), mean elimination half-life ($T_{1/2}$), maximal serum concentration ($C_{max}$), and AUC (area under the curve, i.e. total amount of plasma progesterone observed) derived from the blood samples taken on day 0 of the evaluation are summarized in Table II.

TABLE II

|  | Progesterone dose | |
|---|---|---|
|  | 50 mg (20 subjects) | 100 mg (30 subjects) |
| $T_{max}$ hours | 6.1 ± 2.63 | 6.4 ± 3.35 |
| $T_{1/2}$ (hours) | 13.18 ± 1.3 | 13.7 ± 1.05 |
| $C_{max}$ (nmol/liter) | 20.43 ± 8.01 | 31.61 ± 12.62[a] |
| AUC (nmol/hour/liter) | 154.15 ± 60.31 | 247.61 ± 123.04[b] |

Values are mean ± standard deviation; [a]$P = 0.0004$; [b]$P = 0.001$.

As shown in Table III, after 14 and 30 days of continuous application twice daily, the serum P levels were significantly higher compared to baseline values on day 0. No statistically significant difference in plasma levels of follicle stimulating hormone, leutinizing hormone, estradiol, cortisol, dehydroepiendosterone sulfate, or aldosterone were observed in the study groups between baseline values and after continued administration of the tablets of the invention. Similarly, the plasma levels of serum glutamic oxaloacetic transaminase, alkaline phosphatase, cholesterol, triglycerides, high density lipoprotein, low density lipoprotein, and very low density lipoprotein did not change significantly between the baseline measurement and the measurements at 14 and 30 days of twice-daily administration.

TABLE III

|  | Blood Progesterone levels, nmol/liter | |
|---|---|---|
| Day sample | Progesterone dose | |
| was taken | 50 mg (20 subjects) | 100 mg (30 subjects) |
| Day 0[a] | 1.05 ± 0.7 | 3.0 ± 2.4 |
| Day 14[a] | 17.48 ± 9.8[b] | 26.08 ± 13.96[b] |
| Day 30[a] | 17.38 ± 14.39 | 21.42 ± 16.32 |

[a]$P = 0.0001$, significant difference between progesterone baseline values on day 0 compared to day 14 and day 30;
[b]$P = 0.02$.

EXAMPLE 5

The efficacy of tablets prepared in accordance with the present invention was compared with the efficacy of prior art tablets as follows:

Thirteen healthy, postmenopausal women with intact uteri who were undergoing hormonal replacement therapy (HRT) were given complete medical evaluation by history, physical and gynecological examination, and instructed to discontinue HRT two weeks prior to the comparative trial.

Part A: Single-Dose Pharmacokinetics of Micronized Progesterone in the Form of a Gelatin Capsule (Utrogestan, Produced by Basins-Iscovesco, Paris, France).

Participants received oral ethinyl estradiol (Estrofem, Novo-Nordisk, Denmark), 4 mg per day for 14 days. On day 14 at 8 AM, in a fasting state, an intravenous indwelling catheter was inserted into the cubital vein and blood was drawn for baseline progesterone and estrogen levels. The women were then instructed to self-administer a single gelatin capsule containing 100 mg of micronized progesterone high in the vagina. Repeat blood samples for progesterone concentrations were drawn ½, 1, 2, 4, 6, 8, 10, 12 and 24 hours after the vaginal insertion.

Part B: Single-Dose Pharmacokinetics of Micronized Progesterone in the Form of a Vaginal Tablet According to the Present Invention.

After a washout period of 2 weeks, the same subjects as in Part A were again administered 4 mg or ethinyl estradiol (Estrofem) for 14 days. On day 14 the same procedure as recited in Part A was repeated, except that this time the women were instructed to insert 100 mg of progesterone in the form of an effervescent tablet according to the present invention, using a plastic applicator. Blood samples for progesterone levels were drawn at the same intervals as in Part A.

Samples were assayed using an Immulite enzyme immunoassay (Diagnostic Products Corporation, Los Angeles, Calif.) to measure plasma progesterone (SI conversion factor 3.18; sensitivity 0.2 ng/ml (0.6 nmol/L, inter- and intra-assay coefficients of variation precision<10%)) and estradiol ($E_2$) (SI conversion factor 3.67; sensitivity 12 pg/ml (44 pmol/L, inter- and intra-assay coefficients of variation precision<10%). The pharmacokinetic parameters calculated from the concentration curve were compared between the two study groups by the Wilcoxon 2-sample test, the Kruskal-Wallis test and by analysis of variance (ANOVA). Students T-test was used to compare estrogen levels for the two treatment parts.

Table IV summarizes the baseline details of the of the thirteen women who participated in the study of Example 5.

TABLE IV

|  | Mean ± SD | Median | Minimum | Maximum |
|---|---|---|---|---|
| Age (years) | 52.2 ± 3.6 | 53 | 42 | 57 |
| Weight (kg) | 72 ± 15.4 | 70 | 46 | 100 |
| Height (cm) | 165.1 ± 6.5 | 165 | 155 | 178 |
| BMI (kg/m$^2$) | 263. ± 4.7 | 25.7 | 19.1 | 34.2 |

Data are expressed as mean ± standard deviation unless otherwise specified.
Body mass index (BMI) was calculated as weight in kg divided by the square of height in meters.

The mean peak plasma level ($T_{max}$), mean elimination half-life ($T_{1/2}$), maximal serum concentration ($C_{max}$), and AUC (area under the curve, i.e. total amount of plasma progesterone observed) derived from the blood samples taken on day 0 of the evaluation are summarized in Table V.

TABLE V

|  | Treatment | |
|---|---|---|
|  | Vaginal Tablet | Gelatin Capsule |
| Tmax (hours) | 6.92 ± 3.12 | 6.23 ± 6.56[b] |
| $T_{1/2}$ (hours) | 16.39 ± 5.25 | 22.08 ± 16.5 |
| $C_{max}$ (nmol/l) | 31.53 ± 9.15 | 23.85 ± 9.57[a] |
| AUC (nmol/h/l) | 379.99 ± 137.07 | 325.89 ± 167.78 |

Values are mean ± standard deviation;
[a]P = 0.0472;
[b]Statistically significant difference of variance, P = 0.02.

A single dose of 100 mg micronized progesterone in the form of both gelatin capsules and vaginally administrable tablets in accordance with the present invention resulted in a similar rapid increase in plasma progesterone levels within 2.5-3 hours after administration. The statistically significant difference of variance between the two groups indicates a more predictable $T_{max}$ for the tablets of the present invention than for the prior art gelatin capsules.

It is to be understood that the amounts and proportions of ingredients recited in the foregoing examples are illustrative only, and that these amounts and proportions may be varied within the scope of the invention. For example, the Example 1 the amount of effervescent recited is about 8 wt. % of the tablets which are the final product of the process described in Example 1. However, the effervescent may be omitted in the practice of the invention, or it may be included in an amount of up to about 12 wt. % of the tablet. Preferably the effervescent constitutes between about 5-12 wt. %, more preferably between about 6-8 wt. % of the tablet. Similarly, progesterone may constitute up to about 20 wt. % of the tablet, preferably between about 6-20 wt. %, more preferably between about 8-12 wt. % of the tablet.

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will also be appreciated by persons skilled in the art that the present invention is not limited by what has been particularly shown and described hereinabove. Rather the scope of the invention is defined only by the claims which follow:

What is claimed:

1. A pharmaceutical tablet consisting of dry natural progesterone as an active ingredient, pharmaceutically acceptable excipients, and an effervescent, which tablet dissolves after placement in the vagina and provides a $T_{max}$ from 3.05 hours to 9.75 hours after said tablet is placed in the vagina.

2. A tablet for vaginal administration consisting of natural progesterone, an effervescent, and pharmaceutically acceptable excipients, and prepared by the steps of:
   (i) preparing a mixture consisting of water and the natural progesterone to obtain wetted natural progesterone; and drying said wetted natural progesterone to obtain dry natural progesterone;
   (ii) mixing said dry natural progesterone with at least one pharmaceutically acceptable excipient and an effervescent to form a second mixture; and
   (iii) forming a dry tablet by direct compaction of said second mixture said tablet having the property of dissolving in the vagina and providing a $T_{max}$ from 3.05 hours to 9.75 hours after said tablet is placed in the vagina.

3. A vaginal tablet consisting of natural progesterone, an effervescent, and pharmaceutically acceptable excipients, and prepared by the steps of:
   (i) mixing water with the natural progesterone to obtain wetted natural progesterone in the absence of a pharmaceutically acceptable excipients; and drying said wetted natural progesterone to form dry natural progesterone;
   (ii) mixing said dry natural progesterone with
      (a) pharmaceutically acceptable excipients and
      (b) an effervescent to form a mixture; and
   (iii) forming said tablet in dry form by direct compaction of said mixture, the tablet dissolving in the vagina and providing a $T_{max}$ from 3.05 hours to 9.75 hours after said tablet is placed in the vagina.

4. A vaginal tablet sing consisting of between about 6 to 20 wt. % dry natural progesterone, between about 5 to 12 wt. % effervescent, and pharmaceutically acceptable excipients, the tablet dissolving upon placement in the vagina and providing a $T_{max}$ from 3.05 hours to 9.75 hours after said tablet is placed in the vagina.

5. A tablet according to claim 4, wherein the progesterone in said tablet is present in an amount of between about 8 to 12 wt. %.

6. A tablet according to claim 5, wherein the effervescent in said tablet is present in an amount of between about 6 to 8 wt. %.

7. The tablet of claim 1, wherein the progesterone is micronized progesterone.

8. The tablet of claim 2, wherein the progesterone is micronized progesterone.

9. The tablet of claim 3, wherein the progesterone is micronized progesterone.

10. The tablet of claim 4, wherein the progesterone is micronized progesterone.

11. The tablet of claim 7, wherein the micronized progesterone in said tablet is present in an amount of at least 50 mg.

12. The tablet of claim 7, wherein the micronized progesterone in said tablet is present in an amount of about 50 mg.

13. The tablet of claim 7, wherein the micronized progesterone in said tablet is present in an amount of about 100 mg.

14. The tablet of claim 10, wherein the micronized progesterone in said tablet is present in an amount of at least 50 mg.

15. The tablet of claim 10, wherein the micronized progesterone in said tablet is present in an amount of about 50 mg.

16. The tablet of claim 10, wherein the micronized progesterone in said tablet is present in an amount of about 100 mg.

17. The tablet of claim 1, wherein the effervescent in said tablet is present in an amount of from about 5% to about 12% by weight.

18. The tablet of claim 1, wherein the effervescent in said tablet is present in an amount of about 8% by weight.

19. The tablet of claim 4, wherein the effervescent in said tablet is present in an amount of from about 5% to about 12% by weight.

20. The tablet of claim 4, wherein the effervescent in said tablet is present in an amount of about 8% by weight.

21. A vaginally administrable tablet consisting of dry micronized natural progesterone as an active ingredient, pharmaceutically acceptable excipients and an effervescent, wherein said tablet has the property of dissolving in the vagina and providing a $T_{max}$ from 3.05 hours to 9.75 hours after said tablet is placed in the vagina.

22. A vaginal tablet consisting essentially of dry micronized natural progesterone, colloidal anhydrous silica, maize 1500 starch, povidone 30, lactose, adipic acid, sodium bicarbonate, magnesium stearate, and sodium lauryl sulfate, wherein the tablet has the property of dissolving upon placement in the vagina.

23. The tablet of claim 22, consisting essentially of 8 wt. % dry micronized natural progesterone, 0.2 wt. % colloidal anhydrous silica, 16.8 wt. % maize 1500 starch, 3.9 wt. % povidone 30, 60.8 wt. % lactose, 4.6 wt. % adipic acid, 3.4 wt. % sodium bicarbonate, 1.8 wt. % magnesium stearate, and 60.4 wt. % sodium lauryl sulfate.

24. A vaginal tablet consisting of dry micronized natural progesterone as an active ingredient, pharmaceutically acceptable excipients, and an effervescent.

* * * * *

UNITED STATES PATENT AND TRADEMARK OFFICE
CERTIFICATE OF CORRECTION

PATENT NO.        : 7,393,543 B2
APPLICATION NO.   : 10/832742
DATED             : July 1, 2008
INVENTOR(S)       : Azariah Jossifoff It is certified that error appears in the above-identified patent and that said Letters Patent is hereby corrected as shown below:

Delete Claim 12, at column 11, lines 14 and 15, as an inadvertent duplicate of claim 11.

Delete Claim 14, at column 11, lines 18 and 19, as an inadvertent duplicate of claim 13.

In Claim 23, column 12, line 23, delete "60.4" and insert -- 0.4 --.

Signed and Sealed this

Twenty-fourth Day of November, 2009

David J. Kappos
*Director of the United States Patent and Trademark Office*